United States Patent [19]

Frossard

[11] Patent Number: 4,861,708
[45] Date of Patent: Aug. 29, 1989

[54] RESTRICTION FRAGMENT ANALYSIS OF INDIVIDUALS USING CARDIOVASCULAR SYSTEM PROBES

[75] Inventor: Philippe M. Frossard, Palo Alto, Calif.

[73] Assignee: Biotechnology Research Partners, Ltd., Mountain View, Calif.

[21] Appl. No.: 817,433

[22] Filed: Jan. 9, 1986

Related U.S. Application Data

[63] Continuation-in-part of Ser. No. 796,904, Nov. 12, 1985, abandoned.

[51] Int. Cl.$^4$ .................. C12Q 1/68; G01N 33/48
[52] U.S. Cl. ................................... 435/6; 436/63; 436/501; 436/503; 536/27; 935/11; 935/78; 935/79
[58] Field of Search ............... 435/6, 810; 436/63, 436/94, 501, 503; 536/27; 935/11, 78, 79

[56] References Cited

U.S. PATENT DOCUMENTS 4,623,619 11/1986 Owerbach et al. ............... 435/6

OTHER PUBLICATIONS

Rees, A., et al, "DNA Polymorphism Adjacent to Human Apoprotein A-1 Gene . . . ", The Lancet, Feb. 26, 1983, pp. 444–446.
Fojo, S. S. et al., "Analysis of the Apo C-II Gene . . . ", Biochem Biophys Res. Comm. 124(1), 308–313 (1984).
Wallis, S. C. et al, "The Isolation of a Genomic Clone . . . Apolipoprotein CII Gene . . . ", Hum Genet 68, 286–289 (1984).
Karathanasis, S. K. et al, "An inherited Polymorphism in the Apolipoprotein A-1 Gene . . .", Nature 301, 718–720 (1983).

Primary Examiner—Robert J. Warden
Assistant Examiner—Richard Wagner
Attorney, Agent, or Firm—Irell & Manella

[57] ABSTRACT

Polymorphisms in the renin, kallikrein, and ANF gene regions are predictive for hypertension in individual human subjects.

4 Claims, 4 Drawing Sheets

FIG. 1-1

```
901  TCT ACC AGC TCC ATA GAG AAG CTC ATG GAG GCC TTG GGA GCC AAG AAG AGG CTG TTT GAT  960
     Ser Thr Ser Ser Ile Glu Lys Leu Met Glu Ala Leu Gly Ala Lys Lys Arg Leu Phe Asp
                     (240)                    310                    (250)       320

961  TAT GTC GTG AAG TGT AAC GAG GGC CCT ACA CTC CCC GAC ATC TCT TTC CAC CTG GGA GGC 1020
     Tyr Val Val Lys Cys Asn Glu Gly Pro Thr Leu Pro Asp Ile Ser Phe His Leu Gly Gly
                     (260)                    330                    (270)       340

1021 AAA GAA TAC ACG CTC ACC AGC GCG GAC TAT GTA TTT CAG GAA TCC TAC AGT AAA AAG 1080
     Lys Glu Tyr Thr Leu Thr Ser Ala Asp Tyr Val Phe Gln Glu Ser Tyr Ser Lys Lys
                     (280)                    350                    (290)       360

1081 CTG TGC ACA CTG GCC ATC CAC GCC ATG GAT ATC CCG CGA CCC ACT GGA CCC ACC TGG GCC 1140
     Leu Cys Thr Leu Ala Ile His Ala Met Asp Ile Pro Pro Pro Thr Gly Pro Thr Trp Ala
                     (300)                    370                    (310)       380

1141 CTG GGG GCC ACC TTC ATC CGA ATC TAC ACA GAG TTT GAT CGG AAC CGT 1200
     Leu Gly Ala Thr Phe Ile Arg Ile Tyr Thr Glu Phe Asp Arg Asn Arg Ile
                     (320)                    390                    (330)       400

1201 GGC TTC GCC TTG GCC CGC TGA GGCCCCTCTGCCACCAGGCAGGCCCTGCCTTCAGCCCTGGCCCAGAGCTGGA 1273
     Gly Phe Ala Leu Ala Arg
                     (340)406

1274 ACACTCTCTGAGATGCCCCTCTGCCTGGGCTTATGCCCTCAGATGGAGACATTGGATGTGGAGCTCCTGCTGATGCGT 1352

1353 GCCCTGACCCCTGCACCAGCCCTTCCCTGCTTTGAGGACAAAGAGAATAAAGACTTCATGTTCAC
``` renin 3'

FIG. I-2

```
                                                                80
┌─────────────────────────────────────────────────────────────┐
│ggatccatttgtctcgggctgctggctgcctgccatttcctcctctccaccct│tatttgg
└─────────────────────────────────────────────────────────────┘
                                                               120
aggccctgacagctgagccacaaacaaaccaggggagctgggcaccagcaagcgtcaccc
                                                               180
tctgtttccccgcacggtaccagcgtcgaggagaaagaatcctgaggcacggcggtgaga
                                                               240
taaccaaggactcttttttactcttctcacacctttgaagtgggagcctcttga┌──────┐
                                                       │gtcaaa│
                                                               300
tcagtaagaatgcggctcttgcagctgagggtctgggggctgttggggctgcccaaggc
                                                               360
agagaggggctgtgacaagccctgcggatgataactttaa─┌───────┐cctgctggct
                                         │gggcatct│
                                                               420
tctcacttggcagctttatcactgcaagtgacagaatggggagggttctgtctctcctgc
                                                               480
gtgcttggagagctggggggc┌──────┐aagaggcggcactgggcagctgggagacaggga
                     │tataaa│
                                                               540
cagacgtaggccaagagaggggaaccagagaggaaccagaggggagagacagagcagcaa
                                                               600
gcagtggattgctccttgacgacgccagcATGAGCTCCTTCTCCACCACCACCGTGAGCT
                              MetSerSerPheSerThrThrThrValSerP
                                                               660
TCCTCCTTTTACTGGCATTCCAGCTCCTAGGTCAGACCAGAGCTAATCCCATGTACAATG
heLeuLeuLeuLeuAlaPheGlnLeuLeuGlyGlnThrArgAlaAsnProMetTyrAsnA
                                                               720
CCGTGTCCAACGCAGACCTGATGGATTTCAAGgtagggccaggaaagcgggtgcagtctg
laValSerAsnAlaAspLeuMetAspPheLys
                                                               780
gggccagggggctttctgatgctgtgctcactcctcttgatttcctccaagtcagtgagg
                                                               840
tttatcccttteeetgtattttccttttctaaagAATTTGCTGGACCATTTGGAAGAAAA
                                  AsnLeuLeuAspHisLeuGluGluLy
                                                               900
GATGCCTTTAGAAGATGAGGTCGTGCCCCCACAAGTGCTCAGTGAGCCGAATGAAGAAGC
sMetProLeuGluAspGluValValProProGlnValLeuSerGluProAsnGluGluAl
                                                               960
GGGGGCTGCT┌────────────────────────────────────────────────┐
          │CTCAGCCCCCTCCCTGAGGTGCCTCCCTGGACCGGGGAAGTCAGCCCAGC│
aGlyAlaAlaLeuSerProLeuProGluValProProTrpThrGlyGluValSerProAl
                                                              1020
┌───┐GAGAGATGGAGGTGCCCTCGGGCGGGGCCCCTGGGACTCCTCTGATCGATCTGCCCT
│CCA│
aGlnArgAspGlyGlyAlaLeuGlyArgGlyProTrpAspSerSerAspArgSerAlaLe
                                                              1080
CCTAAAAAGCAAGCTGAGGGCGCTGCTCACTGCCCCTCGGAGCCTGCGGAGATCCAGCTG
uLeuLysSerLysLeuArgAlaLeuLeuThrAlaProArgSerLeuArgArgSerSerCy
                                                              1140
CTTCGGGGGCAGGATGGACAGGATTGGAGCCGAGAGCGGACTGGGCTGTAACAGCTTCCG
sPheGlyGlyArgMetAspArgIleGlyAlaGlnSerGlyLeuGlyCysAsnSerPheAr
                                                              1200
Ggtaagaggaactggggatggaaatgggatgggatggacactactgggagacaccttcag
g
                                                              1260
caggaaagggaccaatgcagaagctcattccctctcaagtttctgccccaacacccagag
                                                              1320
tgccccatgggtgtcaggacatgccatctattgtccttagctagtctgctgagaaaatgc
                                                              1380
ttaaaaaaaaaggggggggggctgggcacggtcgtcacgcctgtaatcccagcactttgg
                                                              1440
gaggccaggcagcggatcatgaggtcaagagatcaagactatcctggccaacatggtgaa
                                                              1500
accccagctctactaaaaatacaaaaattagctgggtgtgtggcgggcacctgtactctc
                                                              1580
agctacttgggaggctgaggcaggagaatcacttgaacccaggaggcagaggttgcagtg
                                                              1620
agcagagatcacgccactgcagtccagcctaggtgatagagcgagactgtctcaaaaaaa
                                                              1680
aaaaaaaaggccaggcgcggtggctcacgcctgtaatcccagcgctttgggaggccaag
```

FIG. 2a-1

```
                                                                1740
gcgggtggatcacgaggtcaggagatggagaccatcctggctaacacggtgaaacccgt
                                                                1800
ctctactaaaaatacaaaaaattagccaggcgtggtggcaggcgcctgtaagtcctagct
                                                                1860
actccggaggctgaggcaggagaatggcgtgaacccgggaggcggagcttgcagtgagca
                                                                1920
gagatggcaccactgcactccagcctgggcgacagagcaagactccgtctcaaaaaaaaa
                                                                1980
aaaaaaaaagcaactgccactagcactgggaattaaatattcatagagccaagttat
                                                                2040
ctttgcatggctgattagcagttcatattcctccccagaattgcaagatcctgaagggct
                                                                2100
taagtgaaatttactctgatgagtaacttgcttatcaattcatgaagctcagagggtcat
                                                                2160
caggctggggtgggggccggtgggaagcaggtggtcagtaatcaagttcagaggatgggc
                                                                2220
acactcatacatgaagctgacttttccaggacagccaggtcaccaagccagatatgtctg
                                                                2280
tgttctctttgcagTACTGAagataacagccagggaggacaagcagggctgggcctaggg
               Tyr
                                                                2340
acagactgcaagaggctcctgtccctggggtctctgctgcatttgtgtcatcttgttgc
                                                                2400
catggagttgtgatcatcccatctaagctgcagcttcctgtcaacacttctcacatctta
                                                                2460
tgctaactgtagataaagtggtttgatggtgacttcctcgcctctcccacccatgcatt
                                                                2520
aaattttaaggtagaacctcacctgttactgaaagtggtttgaaagtgaataaacttcag
                                                                2580
caccatggacagaagacaaatgcctgcgttggtgtgctttctttcttcttgggaagagaa
ttc
```

```
                                   ↓                    -1   1                                                     10
                                       Ala Pro Pro Ile Gln Ser Arg Ile Val Gly Gly Trp Glu Cys Glu Gln His
                                       GCG CCC CCG AUU CAG UCC CGG AUU GUG GGA GGC UGG GAG UGU GAG CAG CAU 20                                                       30
Ser Gln Pro Trp Gln Ala Ala Leu Tyr His Phe Ser Thr Phe Gln Cys Gly Gly Ile Leu
UCC CAG CCC UGG CAG GCG GCU CUG UAC CAU UUC AGC ACU UUC CAG UGU GGG GGC AUC CUG 40                                                                       50
Val His Arg Gln Trp Val Leu Thr Ala Ala His Cys Ile Ser Asp Asn Tyr Gln Leu Trp
GUG CAC CGC CAG UGG GUG CUC ACA GCU GCU CAU UGC AUC AGC GAC AAU UAC CAG CUC UGG 60                                                               70
Leu Gly Arg His Asn Leu Phe Asp Asp Glu Asn Thr Ala Gln Phe Val His Val Ser Glu
CUG GGU CGC CAC AAC UUG UUU GAC GAC GAA AAC ACA GCC CAG UUU GUU CAU GUC AGU GAG 80                                                                       90
Ser Phe Pro His Pro Gly Phe Asn Met Ser Leu Leu Glu Asn His Thr Arg Gln Ala Asp
AGC UUC CCA CAC CCU GGC UUC AAC AUG AGC CUC CUG GAG AAC CAC ACC CGC CAA GCA GAC 100                                                              110
Glu Asp Tyr Ser His Asp Leu Met Leu Leu Arg Leu Thr Glu Pro Ala Asp Thr Ile Thr
GAG GAC UAC AGC CAC GAC CUC AUG CUG CUC CGC CUG ACA GAG CCU GCU GAU ACC AUC ACA 120                                                                      130
Asp Ala Val Lys Val Val Glu Leu Pro Thr Gln Glu Pro Glu Val Gly Ser Thr Cys Leu
GAC GCU GUG AAG GUC GUG GAG UUG CCC ACC CAG GAA CCC GAA GUG GGG AGC ACC UGU UUG 140                                                              150
Ala Ser Gly Trp Gly Ser Ile Glu Pro Glu Asn Phe Ser Phe Pro Asp Asp Leu Gln Cys
GCU UCC GGC UGG GGC AGC AUC GAA CCA GAG AAU UUC UCA UUU CCA GAU GAU CUC CAG UGU 160                                                                      170
Val Asp Leu Lys Ile Leu Pro Asn Asp Glu Cys Glu Lys Ala His Val Gln Lys Val Thr
GUG GAC CUC AAA AUC CUG CCU AAU GAU GAG UGC GAA AAA GCC CAC GUC CAG AAG GUG ACA

180              *                                               190
Asp Phe Met Leu Cys Val Gly His Leu Glu Gly Gly Lys Asp Thr Cys Val Gly Asp Ser
GAC UUC AUG CUG UGU GUC GGA CAC CUG GAA GGU GGC AAA GAC ACC UGU GUG GGU GAU UCA 200                                                                      210
Gly Gly Pro Leu Met Cys Asp Gly Val Leu Gln Gly Val Thr Ser Trp Gly Tyr Val Pro
GGG GGC CCG CUG AUG UGU GAU GGU GUG CUC CAA GGU GUC ACA UCA UGG GGC UAC GUC CCU 220                                                              230
Cys Gly Thr Pro Asn Lys Pro Ser Val Ala Val Arg Val Leu Ser Tyr Val Lys Trp Ile
UGU GGC ACC CCC AAU AAG CCU UCU GUC GCC GUC AGA GUG CUG UCU UAU GUG AAG UGG AUC

238
Glu Asp Thr Ile Ala Glu Asn Ser
GAG GAC ACC AUA GCG GAG AAC UCC UGA
```

15 DNAs digested with BglI and hybridized to the 5' cDNA probe

RESTRICTION FRAGMENT ANALYSIS OF INDIVIDUALS USING CARDIOVASCULAR SYSTEM PROBES

CROSS-REFERENCE TO RELATED APPLICATION

This application is a continuation-in-part of U.S. patent application Ser. No. 796,904, filed 12 Nov. 1985, now abandoned.

TECHNICAL FIELD

The invention relates to the use of genetic polymorphism detection to diagnose presence of, or probability of, disease. More particularly, it relates to the use of these techniques to assess the risk of, and follow familial patterns of, the incidence of hypertension.

BACKGROUND ART

Hypertension is one of the most important public health problems in developed countries. It affects more than 60 million people in the United States alone. The disease, which is defined as an elevation of arterial blood pressure, results in secondary organ damage and a reduced lifespan. It occurs in two forms. Essential hypertension, also called primary hypertension, accounts for 95% of all cases, and is of unknown cause. Secondary hypertension, which constitutes the remaining 5% of the cases found, is associated with known causes, such as primary hyperaldosterism, renal disease, or coarctation of the aorta.

While no direct cause for the majority of hypertension cases have been found, some of the metabolic factors which regulate blood pressure are known. Notable among these are the angiotensin and kallikrein systems, which control vasoconstriction and dilation, and the salt-regulating system, which controls the levels of sodium ion in the bloodstream. The angiotensin system contains a number of critical proteins, prominent among which is renin, a key enzyme in the production of an octapeptide, angiotensin-II, which acts directly to constrict vascular smooth muscles and which also induces the release of aldosterone from the adrenal cortex. The proteins of the kallikrein system influence the level of kinin, a vasodilator. The levels of sodium ion are, on the other hand, regulated by an atrial natriuretic peptide factor (ANF). Renin, kallikrein, and ANF are human proteins of determined amino acid sequence. The genes encoding these proteins have been cloned and expressed. See U.S. Ser. Nos. 616,488, filed 1 June 1984, 719,414, filed 3 Apr. 1985, and 790,813, filed 24 Oct. 1985, all assigned to the same assignee and incorporated herein by reference.

There is, at present, no predictive diagnosis for hypertension, nor is there any accurate diagnosis for the various causes of hypertension. It is singularly important to have a predictive tool in the case of this disease, as various preventive therapies, based, for example, on control of the above-mentioned factors, are available. In addition, in relatively benign cases, even regulation of diet, lifestyle, or other noninvasive practices are effective in minimizing risk.

A technique that inherently offers the advantages of early detection, if its results can be effectively correlated with the disorder to be assessed, is genetic analysis. Since the genomic characteristics of an individual are basically determined, it is assumed, at conception, genetic aberrations which are indicia of later metabolic disorders are an ideal early diagnosis tool. Genetic testing can be routinely conducted using present methodology, as early as the seventh week of fetal life. In adults and children, it can be accomplished using a small blood sample. Over the last ten years, the availability of restriction enzymes and DNA probing techniques has made possible the use of "restriction fragment length polymorphisms" (RFLPs) in such diagnosis. Using the, by now, well established Southern blot hybridization technique (Southern, E., *J Mol Biol* (1975) 98:503–517), it has been possible successfully to diagnose sickle cell anemia (Kan, Y. W., et al, *Proc Natl Acad Sci (USA)* (1978) 75:5631); β-thalassemia (Antonarakis, S. E., et al, *Proc Natl Acad Sci (USA)* (1983) 79:137); type II diabetes (Rotwein, P., et al, *Science* (1981) 213:1117); familial growth hormone deficiency (Phillips, J. A., III, *Banbury Report* 14, Cold Spring Harbor Laboratory (1983) pp 305–315); phenylketonuria (Woo, S. L. C., et al, *Nature* (1983) 306:151); Huntington's disease (Gusella, J. F., et al, *Nature* (1983) 306:234); and hemophilia B (Gianelli, et al, *Lancet* (1984) i:239, Grunenbaum, et al, *J Clin Invest* (1984) 73:1491).

The use of genetic detection systems is particularly appropriate in predicting the incidence of hypertension for an individual since it appears that genetic, rather than environmental, factors are in large part responsible for the onset of the disease. This has been shown in both animal and human studies, including of blood pressures which exist as patterns or "aggregations" within families. Adopted children do not demonstrate familial aggregation of blood pressures. Therefore, an assessment of the genome of the subject provides fertile ground for assessment of risk.

All of the successful predictive tests listed above are grounded in identification of a particular polymorphism or polymorphisms which correlates with the disease or disorder in question. It has been calculated that the number of polymorphisms expected in the human genome should be of the order of $10^7$, based on an assumed probability of 0.005 for a given nucleotide to be polymorphic; this number being inferred from studies of the human growth hormone, αl-antitrypsin and β-like globin gene cluster loci (Jeffreys, A. J., *Cell* (1979) 18:1–10; Oster, H., et al, *Am J Hum Gen* (1984) 36(suppl) 150S). The challenge is to determine which of these over ten million polymorphisms is associated with a particular disorder, and to devise a procedure to detect it.

The present invention uses the gene loci associated with the production of renin, of ANF, or of kallikrein as sites for the occurrence of polymorphisms associated with hypertension.

The availability of the appropriate DNA sequences has made this a feasible approach. Human renin cDNA and genomic DNA have been described by Hardmann, J. A., et al, *DNA* (1984) 3:457; Imai, T., et al, *Proc Natl Acad Sci (USA)* (1983) 80: 7405; Hobart, P. M., et al, *Proc Natl Acad Sci (USA)* (1984) 81: 5026; Miyazaki, H., et al, *Proc Natl Acad Sci (USA)* (1984) 81: 5999. DNA encoding human ANF has been described by Greenberg, B. D., et al, *Nature* (1984) 312:656–658; Yamanaka, N., et al, *Nature* (1984) 309: 719; Maki, M., et al, *Nature* (1984) 309: 722; Oikawa, S., et al, *Nature* (1984) 309: 724; Seidman, C. E., et al, *Science* (1984) 225: 324; Zivin, R. A., et al, *Proc Natl Acad Sci (USA)* (1984) 81: 6325. The cDNA sequence encoding human kallikrein is disclosed in U.S. Ser. No. 790,813, filed 24 Oct. 1985 (supra).

The present invention provides a number of polymorphic sites in the above-mentioned gene regions which are useful both alone and in combination in predicting the incidence of hypertension by means of a simple blood test.

DISCLOSURE OF THE INVENTION

The invention provides identification of polymorphisms which are predictive of the subsequent development of hypertension and others which are indicative of an individual protected against development of this disease. These polymorphisms are found in the regions of the genome which encodes renin, ANF, and kallikrein. Taken together or in subsets, they provide an identity profile of a particular individual, thus providing a means to follow family inheritance patterns and to assess relationships between individuals in accordance with the familial aggregation of this symptomology. In addition, since these polymorphisms are located in the genomic sequences which regulate blood pressure, is is probable that their pattern of presence or absence will show some additional specific, as yet unknown, correlation to symptomology.

Thus, in one aspect, the invention is directed to a method of predicting the likelihood of development of hypertension in an individual, which method comprises detecting the presence or absence of one or more polymorphisms in the renin, ANF, or kallikrein-encoding gene regions. (Polymorphism refers, in the context of the present invention to a location in the DNA of the genome which is different in various individuals. Usually, for a given location in the genome where such polymorphism occurs, a majority of alleles present in a population of individuals will be of one form, and a minority of the alleles present in the population will be of another. For convenience, and for want of a better general term, the form found in the *minority* of better general term, the form found in the minority of alleles will be referred to as "the polymorphism", using the form present in the majority as a reference. This is in analogy to the manner in which, for example, the term "isotope" is often used to refer to the less common nuclides of an element.)

Specifically, the invention includes:

detecting the presence of absence of a 5 kb or of a 9 kb BglI digestion fragment hybridizing to renin 5' probe, or its substantial equivalent; and/or detecting the presence or absence of a 20 kb or of a 24 kb BglII digestion fragment hybridizing to a renin 5' or renin 3' probes, or their substantial equivalents; and/or detecting the presence or absence of a 6.2 kb or of a 9.0 kb HindIII digestion fragment hybridizing to renin 3' probe or its substantial equivalent; and/or detecting the presence or absence of a 9.8 kb or of a 11 kb TaqI digestion fragment hybridizing to renin 5' or renin 3' probes, or their substantial equivalents; and/or detecting the presence or absence of a 1.4 kb or of a 1.8 kb BanII digestion fragment hybridizing to a mixture of the "3 oligo" probes, or their substantial equivalents; and/or detecting the presence or absence of a 4.1 kb or of a 6.2 kb BglI digestion fragment hybridizing to a mixture of the "3 oligo" probes, or their substantial equivalents; and/or detecting the presence or absence of a 9.1 kb or of a 6.5 kb BglII digestion fragment hybridizing to a mixture of the "3 oligo" probes, or their substantial equivalents; and/or detecting the presence or absence of a 5.2 kb or of a 11.8 kb EcoRI digestion fragment hybridizing to a mixture of the "3 oligo" probes, or their substantial equivalents; and/or detecting the presence or absence of a 15 kb or a 10 kb EcoRI digestion fragment hybridizing to λHK1 probe or its substantial equivalent; and/or detecting the presence or absence of a 3.1 kb PstI digestion fragment hybridizing to λHK1 probe or its substantial equivalent; and/or detecting the presence or absence of a 6 kb DraI digestion fragment hybridizing to λHK1 probe or its substantial equivalent; and/or detecting the presence or absence of a 5 kb NciI digestion fragment hybridizing to λHK1 probe or its substantial equivalent; and/or detecting the presence or absence of a 9 kb NsiI digestion fragment hybridizing to λHK1 probe or its substantial equivalent; and or detecting the presence or absence of a 1 kb MboI digestion fragment hybridizing to λHK1 probe or its substantial equivalent; and/or detecting the presence or absence of a 8 kb Tth111I digestion fragment hybridizing to λHK1 probe or its substantial equivalent; and/or detecting the presence or absence of a 4.5 kb StuI digestion fragment hybridizing to λHK1 probe or its substantial equivalent.

In still another aspect, the invention relates to determination of a genetic fingerprint of a subject which relates to cardiovascular disorders using polymorphisms of the renin, kallikrein, and/or ANF gene region. The invention is also directed to kits suitable for performing the methods of the invention.

BRIEF DESCRIPTION OF THE DRAWINGS

FIG. 1 shows the DNA sequence of the renin 5' and renin 3' probes.

FIG. 3 shows the DNA sequence of the λHK1 probe.

MODES OF CARRYING OUT THE INVENTION

In the description below, distances of polymorphisms from reference points and lengths of deletions are given, when known, in bp or kb. Where the sequence is known, such measures can be quite precise, but when assessed by measuring fragment sizes on gels or by other experimental means, these measures contain a margin of uncertainty, as is well understood in the art. In general, for measures of >4 kb, the margin of uncertainty is $\pm \sim 0.3$ kb; for smaller lengths, the error is $\pm \sim 10\%$.

A. TECHNIQUES FOR DETECTION OF POLYMORPHISMS

Application of the method of the invention to predict potential hypertensive individuals or to obtain a genetic "fingerprint" based on some or all of the polymorphisms associated with the general genomic renin, kallikrein, and ANF regions, employs standard techniques of DNA extraction, purification, restriction enzyme digestion, and size separation. Techniques for hybridization with probe and detecting successfully hybridized substrate arranged according to molecular weight are also well known to those in the art. The general approach to finding and detecting the significant polymorphisms is the following:

DNA is extracted from the somatic cells of the individual to be tested, for example from leukocytes, placental cells, cultured fibroblasts, or, in the case of fetal individuals, from cells of the amniotic fluid. In ordinary circumstances, the test material comprises leukocytes from a blood sample—25-50 ml blood yields 200-400 μg DNA. The high molecular weight DNA fraction is separated, and subjected to treatment with a particular, selected restriction enzyme, such as, for example, EcoRI, BamHI, MstI, XmnI, and the like. After digestion of the high molecular weight DNA, the digest is applied to a polyacrylamide or agarose gel and subjected to electrophoresis to obtain separation of the DNA fragments resulting from restriction enzyme digestion into positions on the gel determined by the size (length) of the fragment. The contents of the gel are then replicated by transferring to a nitrocellulose filter or other suitable matrix for use as a probe hybridization support. The DNA fragments, either before or after transfer to the nitrocellulose filter replica, are treated with a denaturant such as sodium hydroxide/salt. The denatured, single-stranded DNA, replicated electrophoresis patterns are probed with labeled (usually by $^{32}P$) single-stranded DNA fragments. Other labels beside radioactivity, such as fluorescent molecules may also be used.

Depending on the probe selected, fragments will be detected which derive from a particular region on the genome. For example, in the method of the invention, a cDNA sequence from the renin, kallikrein, or ANF gene sequences is used as a probe. Therefore, the only fragments which will appear on the hybridized filters are those which will contain sequences complementary to this probe—i.e., only those which have not been severed either in the genome itself or by the restriction enzyme cleavage from the complementary renin, kallikrein, or ANF fragment. Stated in another way, by using a particular probe, alterations in the genome which are proximal to sequences corresponding to that probe are detected.

The specific procedures used in the general process described in the preceding paragraphs are understood in the art. Procedures for DNA extraction from somatic cells may, for example, be found in Kan, Y. W., et al, *Proc Natl Acad Sci (USA)* (1978) 75:5631-5635; Taylor, J. M., et al, *Nature* (1984) 251:392-393; and Kan, Y. W., et al, *N Eng J Med* (1977) 297:1080-1084. Further improvements which permit rapid extraction of the DNA are also disclosed by Law, D. G., et al, *Gene* (1984) 28:153-158. Techniques for size separation of the restriction enzyme treated DNA fragments are also described in the foregoing references. Restriction enzyme digestions are generally standard in the art and are carried out under buffer, ionic strength, and temperature conditions which are specified by the manufacturer of the particular restriction enzyme.

Transfer to nitrocellulose or other support and probing by prehybridization with nonspecific DNA followed by hybridization with labeled probe are also standard procedures disclosed, for example, in the foregoing references and by Southern, E., (supra). The section of the genome which is fingerprinted or otherwise subject to study using the results is, of course, dependent on the nature of the probe. The probes useful in the present invention are selected from the renin, kallikrein, or ANF gene.

B. NATURE OF THE GENE REGIONS AND PROBES USEFUL IN THE INVENTION

The fragment pattern obtained is diagnostic for a particular polymorphism if the probe selected is complementary to a DNA sequence sufficiently proximal to the polymorphism on the genome that it is not severed from the polymorphism by the restriction cleavage, and has a low probability of being segregated from the polymorphism by crossing over. Acceptable distance limits between the region of probe complementarity and the polymorphism are therefore arbitrary. Generally, probes which hybridize to DNA sequences within 10 kb upstream or downstream of the polymorphism give acceptable results. Occasionally, the pattern of restriction enzyme cleavage may place a distal probe hybridization site on a fragment irrelevant to the polymorphism. The closer the probe to the polymorphism, the greater the range of usable restriction enzymes.

Accordingly, as used herein, a probe which is a "substantial equivalent" to a specified probe is one which hybridizes to the same fragment length in digests of DNA from individuals with a particular polymorphism when the same restriction enzyme is used. Thus, for the "BglII" polymorphism of the renin gene, when BglII digestion is used for diagnosis, the renin 5' and renin 3' probes (described below) are equivalent. For HindIII digestion, they are not. (Of course, the designated probe can be modified in a trivial manner by being made longer or shorter or by selecting a slightly displaced sequence, and the modified probe will be a substantial equivalent.)

cDNA probes are labeled by nick translation using α [$^{32}P$] dCTP and a α [$^{32}P$] dGTP. Oligomer probes are labeled by kinasing. cDNA probes which are complementary only to the exon regions of the gene and which span over intron regions are workable in the method of the invention.

Probes which hybridize to the renin, kallikrein, and ANF regions of the genome were selected because of the known relationship between the products of these genes and blood pressure.

Renin is a critical protein in the angiotensin system, which controls vasoconstriction/dilation. In this system, the vasoactive agent is angiotensin-II, an octapeptide which acts directly to constrict vascular smooth muscle and to induce the release aldosterone from the adrenal cortex. The level of angiotensin-II is determined by the balance between its rate of inactivation by angiotensinases and its rate of formation in a two step process from angiotensinogen. The rate-limiting step in the conversion of angiotensinogen to angiotensin-II is the step catalyzed by renin—the conversion of angiotensinogen to angiotensin-I. The second step is mediated by a "converting enzyme". Renin is secreted in vivo by the juxtaglomerular cells of the kidney, and is synthesized as a prorenin precursor, which is then processed to give the active renin form. The involvement of renin in the regulation of blood pressure has been established by the utility of inhibitors of renin secretion or direct renin inhibitors. See, for example, Haber, E., *Hypertension and the Angiotensin Systems: Therapeutic Approaches* (1984) Raven Press, 133-145; Gagnol, J. P., et al, *Abstracts International Society of Hypertension* (1984) 10:376.

The ANF gene is also considered a relevant portion of the genome in controlling hypertension since the atrial natriuretic factor produced by this gene controls the excretion of salt from the system. The relationship between high salt and high blood pressure is well established. Therefore, factors which control the level of sodium ion in the system are relevant also to the control of blood pressure.

The kallikrein region is relevant, since the product of this gene is a protein catalyzing the conversion of kininogen to kinin, a known vasodilator. Indeed, kallikrein has been used by injection in the treatment of cardiovascular and cerebrovascular disease, and the urinary excretion of kallikrein is reduced in essential hypertension. Review of the influence of the kallikrein/kinin system on blood pressure are found in Lavinsky, N. G., *Circ Res* (1979) 44: 441–451; and Carretero, O. A., et al, *M J Physiol* (1980) 238: F247–F255.

C. POLYMORPHISMS RELEVANT TO HYPERTENSION

C.1 Polymorphisms of the Renin Gene Region

Two probes have been used to detect polymorphisms in the region of the renin gene, the renin 5′ and the renin 3′ probe. Of course, other equivalent probes can be used, including simple modifications of the exemplified probes, which are constructed by shortening or lengthening the probe sequences or by making minor alterations in the base sequence which do not significantly affect the hybridizing power of the probe. In addition, probes which represent DNA sequences which are slight displacements of the exemplified probes in the genome are also usable.

The renin 5′ probe represents the codons for the first 198 amino acids of the mature renin sequence, and includes the codons for the amino acids of the presequence. The renin 3′ probe contains the remaining mature protein codons. It will be recalled that the labeling process fragments the probe, and thus the presence of intron regions in the target gene does not undermine the effectiveness of the probes.

Four polymorphisms of the renin region have been identified. These are designated BglI, BglII, HindIII, and TaqI in ¶E.2. Correlations of such polymorphisms with hypertension are analyzed as follows:

The findings are interpreted in terms of the relative risk of persons having the polymorphism to show the disease, compared to those having an absence of the polymorphism. These "relative incidence" values are calculated according to Wolf, B., *Ann Hum Genet* (1955) 19:251. As applied to the assays for propensity for hypertension, the relative incidence is calculated as equal to:

(PP×CN)/(PN×CP)

where
- PP is the number of hypertensive patients having the polymorphism;
- PN is the number of hypertensive patients not having the polymorphism;
- CP is the number of controls having the polymorphism;
- CN is the number of controls not having the polymorphism.

The value calculated by this ratio, if significantly greater than 1, indicates that the persons having the polymorphism are at a greater risk of having hypertension; a value less than 1 shows protection against hypertension.

C.2 Polymorphisms of the ANF Region

Figure 2A:
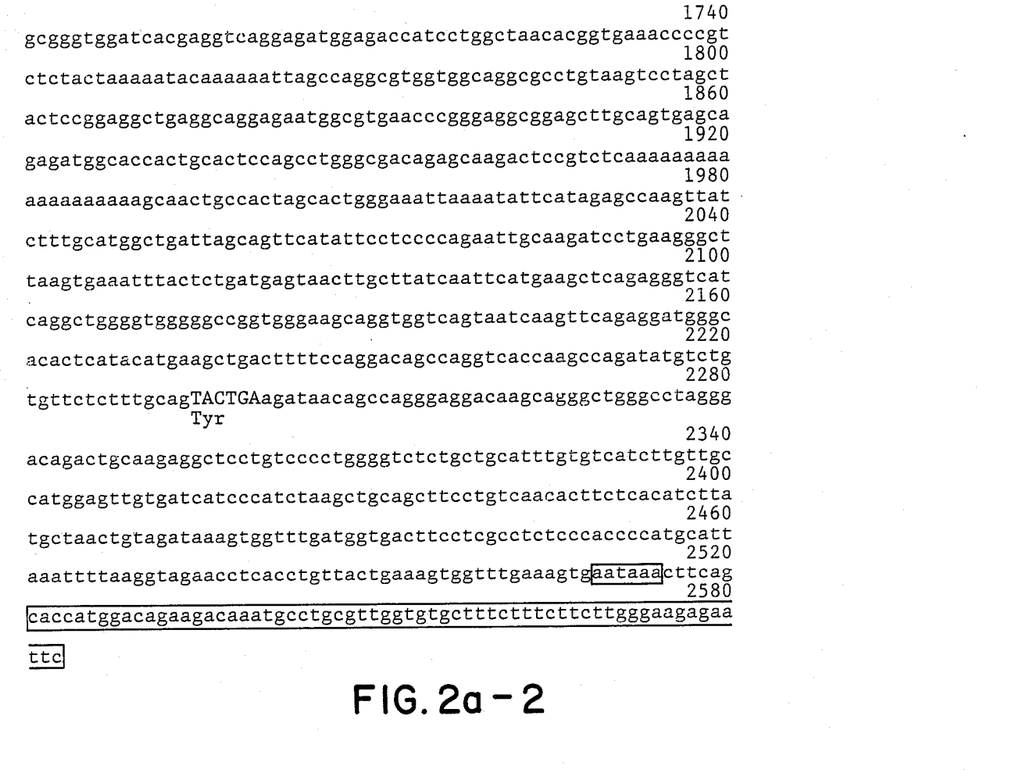
FIG. 2 shows the DNA sequence of the ANF "3-oligo" probes.
Figure 2B:
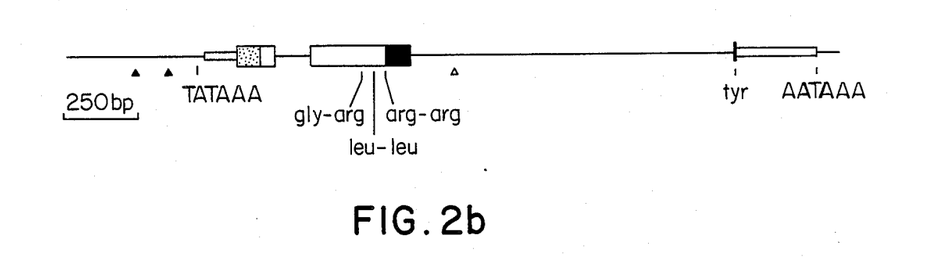

Four polymorphisms have been found in the ANF region, using a mixture of 3 oligomeric probes corresponding to three regions of the ANF gene, as shown in FIG. 2. They are designated BanII, BglI, BglII, and EcoRI in ¶E.3 below. Correlation to hypertension is established as set forth in ¶C.1 above.

C.3 Polymorphisms of the Kallikrein Region

A cDNA probe containing the entire coding sequence for human kallikrein, designated λHKl, was used to probe the kallikrein region. Nine polymorphisms of the kallikrein region, designated EcoRI-A, EcoRI-B, PstI, DraI, NciI, NsiI, MboI, TthlllI, and StuI, have been identified as set forth in the examples below, and their correlation to hypertension is established as set forth in ¶C.1 above.

D. Kits

The reagents suitable for applying the method of the invention to detect the appropriate polymorphisms may be packaged into convenient kits providing the necessary materials, packaged into suitable containers, and, optionally, suitable containers or supports useful in performing the assay. The essential components of the assay include the restriction enzyme associated with the polymorphism, and a suitable probe. Additionally, packages containing concentrated forms of reagents used for hybridization, prehybridization, DNA extraction, etc. may be included if desired. In particular, however, labeled probe, or reagents suitable to form conveniently labeled probe, are useful in facilitating the conduct of the method of the invention.

E. EXAMPLES

The following examples are specific with respect to the probes exemplified and with respect to the precise conditions of DNA extraction, probe hybridization, etc. It is understood that these factors are illustrative but not limiting. The essential features of the invention as it relates to detection of a particular polymorphism are (1) the selection of enzyme, and (2) the selection of probe. For a particular restriction enzyme, a number of substantially equivalent probes which are not segregated from the identified fragment by this restrictions cleavage are usable. Alternatively, other restriction enzymes may be used in conjunction with a probe which hybridizes in particularly close proximity to the polymorphism.

In the above sense, the particular restriction enzyme and cDNA probe chosen are arbitrary. However, it should be noted, as is understood in the art, that the efficacy of the probe is enhanced as it moves closer to the site of the polymorphism. Otherwise, additional cleavage points may be encountered between the polymorphism and the probe, and also the probing site may be separated from the site of the polymorphism during replication by crossing-over events.

E.1. Procedures for Analysis

Leukocytes were obtained from freshly drawn blood collected from each of the human subjects, and high molecular weight genomic DNA was isolated by the procedure of Law, D. J., et al, *Gene* (1984) 28:153–158.

High molecular weight DNA was divided into portions and each was digested to completion with one of the various restriction enzymes under conditions recommended by the suppliers (New England Biolabs and Bethesda Research Laboratories). The digests were electrophoresed in horizontal agarose gels in 30 mM NaH$_2$PO$_4$, 36 mM Tris, 1 mM EDTA, pH 7.7. After electrophoresis, DNA fragments were denatured in situ in 0.5M NaOH/1.5M NaCl for 2×10 min, neutralized in 1M ammonium acetate pH 7.2 for 2×10 min, and transferred overnight onto nitrocellulose paper (Schleicher and Schuell). The filters were rinsed in 2×SSC (1×SSC is 0.15M NaCl, 0.015M sodium citrate pH, 7.4) and baked for 2 hr at 80° C. in vacuo and then were prehybridized for 5 hr in plastic bags using 0.3 ml/cm$^2$ of a solution containing 5×SSPE (1×SSPE is 10 mM Na phosphate pH 7.4, 0.18M NaCl and 1 nM EDTA) containing 5×Denhardt's solution (1×Denhardt's contains 0.2 mg/ml each of Ficoll, polyvinylpyrrolidone and bovine serum albumin), 40% (vol/vol) formamide, and 250 µg/ml sheared and denatured salmon sperm DNA, and hybridized overnight in the same bag in 0.1 ml/cm$^2$ of 5×SSPE, 1×Denhardt's solution, 40% (vol/vol) formamide, 10% dextran sulfate, and 100 µg/ml sheared and denatured salmon sperm DNA, mixed with 100 ng per bag (containing 1 or 2 filters) of the appropriate $^{32}$P-labeled probe, as discussed below. Prehybridization and hybridization were performed at 42° C.

Filters were then washed twice at room temperature in 2×SSC and twice at 65° C. in 2×SSC, 1×Denhardt's solution. DNA sequences hybridized to the $^{32}$P-labeled probes were visualized by autoradiography using XAR-5 films (Kodak) and Cronex intensifying screens (Dupont) at −70° C. for 18 hr to 2 days.

Two specific probes are used for the renin region in the illustrations below: renin 5' probe and renin 3' probe, as shown in FIG. 1.

A mixture of three oligomeric probes was used for the ANF region: a 53-mer corresponding to a sequence at the 5' end, a 50-mer corresponding to a sequence at the middle of the gene and a 63-mer corresponding to a sequence at the 3' end. These oligomers are shown in FIG. 2.

A probe designated λHK1 was used for the kallikrein region. The sequence of this probe is shown in FIG. 3.

The methods used to prepare these probes are described; however, the complete DNA sequences are given so that synthetic methods may also be used. Methods to obtain entire gene sequences, once the desired sequence is known, are now available. See, e.g., Edge, M. D. et al, *Nature* (1981) 292: 756; Nambiar, K. P., et al, *Science* (1984) 223: 1299; or Jay, E., et al, *J. Biol Chem* (1984) 259: 6311.

For use in hybridization, the probes are labeled to a specific activity of 2.0–5.0×10$^8$ cpm/µg by nick-translation, using the BRL nick translation kit (Bethesda Research Laboratories) under recommended conditions with α [$^{32}$P] dCTP (800 Ci/mM; Amersham Corporation) in the presence of unlabeled dATP and dTTP. The probes were denatured just before the hybridization step by incubation for 5 min in a boiling water bath, followed by rapid cooling in ice water.

To prepare the renin probes, a cDNA library was prepared from oligo-dT-primed polyA+ RNA, purified from the kidney of a human accident victim. The cDNA library was constructed in the bacteriophage vector λgt10 and probed with appropriate fragments of Charon-4 human renin genomic clones which had been obtained from a human genomic library by probing with mouse submaxillary gland renin cDNA fragments.

The λgt10 library was prepared by standard procedures which include obtaining double-stranded cDNA from the mRNA, blunt-ending the cDNA with DNA polymeraseI (Klenow), adding commercially available EcoRI linkers, cleaving with EcoRI, and ligating the fragments into EcoRI-digested λgt10 vectors. Two positively responding cDNA clones together, when sequenced using the dideoxy method of Sanger (supra), were shown to contain the entire renin-encoding sequence and 3' untranslated region except for a missing 7 base pairs at the 5' end of the signal sequence. The two clones include 1211 bp of coding region, followed by the entire 3' 198 bp untranslated region, followed, in turn, by a polyA tail. The assignment of the sequence to the appropriate preprorenin codons and reading frame was made by comparison to the published Imai et al (supra) sequence. Two cloned fragments result because of the unique EcoRI site at position 762, as shown in FIG. 1.

The cDNA sequences encoding the preprorenin protein were transferred into pUC9 as the two EcoRI inserts to obtain the cloned vectors pHR1 containing renin 5' probe and pHR2 containing renin 3' probe. pHR1 and pHR2 were prepared by excising the cDNA from λgt10 using EcoRI and ligating each of the resulting fragments into EcoRI-cleaved pUC9. For use as probes, the inserts were removed with EcoRI and labeled.

The ANF probes were prepared from the 2.6 kb genomic clone which encompasses the entire human prepro-ANF gene, as described in Greenberg, G. D., et al, *Nature* (1984) 312:656–658. This clone has been shown to contain Alu family repetitive sequences as shown in FIG. 2. The sequences corresponding to the three probes is shown in the figure—each oligomer corresponds to a different portion of the gene. These probes can be used singly or as a mixture.

The kallikrein probe was prepared from a human kidney cDNA library constructed in λgt10 in a manner precisely analogous to that set forth above. This library was probed with P-32-labeled mouse cDNA clone pMK1, described by Mason et al, *Nature* (1983) 303: 300–307, under conditions of reduced stringency (5×SSC, 50° C.). Twenty positively hybridizing clones were isolated after screening approximately 200,000 recombinant phage. All of the positively hybridizing phage were rescreened by hybridization with a 52-mer oligonucleotide which was based on the amino terminal sequence of human urinary kallikrein (Lottspeich et al, *Hoppe Seyler's Z Physio Chem* (1979) 360: 1947–1950) using codon choices from previously sequenced human genes. A clone designated λHK1 containing the largest (approximately 1 kb) insert was selected and subcloned into M13mp8 for DNA sequencing. The relevant DNA sequence of this clone is shown in FIG. 3. This 1 kb insert was subcloned into pUC8 for amplification, and removed by digestion with EcoRI for denaturation and use as a probe.

E.2 Polymorphisms of the Renin Gene

Using the renin 5' and renin 3' probes, 68 individuals were tested for polymorphism by the procedure of ¶ E.1 above. The following polymorphisms were found, as shown in Table 1.

TABLE 1

| Polymorphism | Probe | Enzyme | More common Fragment | Less common Fragment | Freq |
|---|---|---|---|---|---|
| BglI | renin 5' | BglI | 9 kb | 5 kb | 0.39 |
| BglII | renin 5' | BglII | 20 kb | 24 kb | 0.28 |
| HindIII | renin 3' | HindIII | 9.0 kb | 6.2 kb | 0.34 |
| TaqI | renin 5' renin 3' | TaqI | 9.8 kb | 11.0 kb | 0.22 |

Frequency in this case as in all others is determined as follows: Each individual has two copies of each chromosome; therefore, at any locus or position on the chromosome each person has two "alleles". If these two alleles are identical, the individual is "homozygous" at this locus; if the two alleles are different, he is heterozygous at this locus. Genetic variation between populations can be quantified using the concept of allele frequency, the proportion of all alleles in a population at the locus that are a particular allele. The frequency of any particular allele in a sample is therefore equal to twice the number of homozygotes for that allele plus the number of heterozygotes for that allele divided by two times the number of individuals in the sample.

For example, in the case of the BglI (5 kb/9 kb) polymorphism there were:
28 homozygotes of the 9 kb type
13 homozygotes of the 5 kb type
27 heterozygotes The polymorphic allele frequency (5 kb type) is thus:

$$p = \frac{26 + 27}{56 + 26 + 54}$$

or approximately 0.39.

Figure 4:
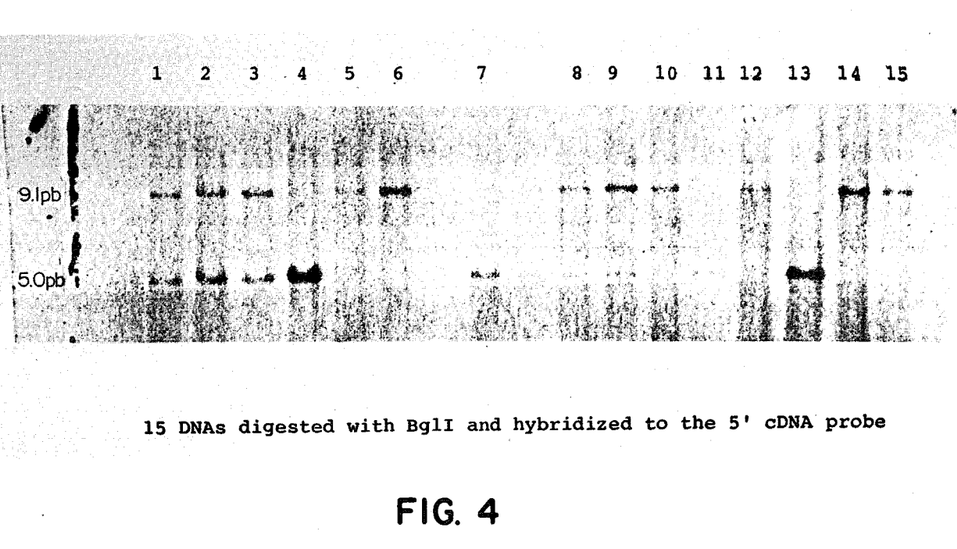
FIG. 4 shows an autoradiogram performed using BglI-digested DNAs from 15 individuals, which digests have been probed by renin 5' cDNA.

Typical results are shown for the BglI polymorphism in FIG. 4. Each lane of the autoradiogram shows the results for one individual probed with renin 5' probe. Lanes 4, 7, 11 and 13 show individuals homozygous for 5 kb fragment, lanes 5, 6, 10, 12, 14, and 15 show individuals homozygous for the 9 kb fragment, and lanes 1–3, 8 and 9 show the results for heterozygous individuals.

E.3 Polymorphisms of the ANF Gene

There are four known polymorphisms of the ANF gene, as shown in Table 2.

TABLE 2

| Polymorphism | Probe | Enzyme | More common Fragment | Less common Fragment | Freq |
|---|---|---|---|---|---|
| BanII | 3 oligo mixture | BanII | 1.8 kb | 1.4 kb | 0.2 |
| BglI | 3 oligo mixture | BglI | 6.2 kb | 4.1 kb | 0.15 |
| BglII | 3 oligo mixture | BglII | 6.5 kb | 9.1 kb | 0.06 |
| EcoRI | 3 oligo mixture | EcoRI | 11.2 kb | 5.2 kb | 0.05 |

The correlation between the presence of the polymorphism above and risk of hypertension is evaluated as set forth in ¶C.1 with respect to the polymorphisms of the renin gene.

E. 4 Polymorphisms of the Kallikrein Gene

Nine polymorphisms were found in the kallikrein gene as shown in Table 3. All polymorphisms in Table 3 were detected with the λHK1 probe.

TABLE 3

| Polymorphism | Enzyme | More common Fragment | Less common Fragment | Freq |
|---|---|---|---|---|
| EcoRI-A | EcoRI | 9.0 kb | 15.0 kb | 0.08 |
| EcoRI-B | EcoRI | 9 kb | 10.0 kb | 0.10 |
| PstI | PstI | ? | 3.1 kb | 0.13 |
| DraI | DraI | 7 kb | 6 kb | 0.05 |
| NciI | NciI | 7 kb | 5 kb | 0.10 |
| NsiI | NsiI | 8 kb | 9 kb | 0.05 |
| MboI | MboI | 2 kb | 1 kb | 0.15 |
| TthlllI | TthlllI | 6 kb | 8 kb | 0.20 |
| StuI | StuI | ? | 4.5 kb | 0.03 |

Correlations with specific symptomologies are obtained as set forth above in ¶C.1.

CONCLUDING REMARKS

Several of the approximately 10 million polymorphisms existent in the human genome have been shown to be useful predictors of individuals at risk for hypertension. These polymorphisms are detectable as fragments of predictable size obtained by digestion of the genomic DNA of the subject individual with a specified restriction enzyme and probing with specific DNA sequences herein described. The availability of this tool for early diagnosis of individuals at risk for hypertension permits the early application of therapeutic measures to prevent the fatal symptomology of the disease.

I claim:

1. A method of genetically identifying an individual, which method comprises:
    obtaining a sample of genomic DNA from said individual;
    digesting said DNA with a restriction endonuclease selected from the group consisting of BglI, BglII, TaqI to provide DNA fragments;
    hybridizing said DNA fragments with renin 5' probe or a substantial equivalent;
    detecting the presence or absence of hybridized polymorphic DNA fragments to provide a set of hybridized fragments characteristic of said individual.

2. A method of genetically identifying an individual, which method comprises:
    obtaining a sample of genomic DNA from said individual;
    digesting said DNA with a restriction endonuclease selected from the group consisting of BglII, HindIII, TaqI to provide DNA fragments;
    hybridizing said DNA fragments with renin 3' probe or a substantial equivalent;
    detecting the presence or absence of hybridized polymorphic DNA fragments to provide a set of hybridized fragments characteristic of said individual.

3. A method of genetically identifying an individual, which method comprises:
    obtaining a sample of genomic DNA from said individual;
    digesting said DNA with a restriction endonuclease selected from the group consisting of BANII, BglI, BglII, EcoRI to provide DNA fragments;
    hybridizing said DNA fragments with ANF "3-oligo" mixture probe or a substantial equivalent;

detecting the presence or absence of hybridized polymorphic DNA fragments to provide a set of hybridized fragments characteristic of said individual.

4. A method of genetically identifying an individual, which method comprises:
obtaining a sample of genomic DNA from said individual;
digesting said DNA with a restriction endonuclease selected from the group consisting of EcoRI, PstI, DraI, NciI, NsiI, MboI, TthlllI, and StuI to provide DNA fragments;
hybridizing said DNA fragments with λHK1 probe or a substantial equivalent;
detecting the presence or absence of hybridized polymorphic DNA fragments to provide a set of hybridized fragments characteristic of said individual.

* * * * *

UNITED STATES PATENT AND TRADEMARK OFFICE
CERTIFICATE OF CORRECTION

PATENT NO.   : 4,861,708

DATED        : August 29, 1989

INVENTOR(S) : Philippe M. Frossard, Palo Alto, Calif.

It is certified that error appears in the above-identified patent and that said Letters Patent is hereby corrected as shown below:

On the title page:

Please correct Assignee as follows:

California Biotechnology Inc.,
   Mountain View, California

Signed and Sealed this

Sixteenth Day of October, 1990

Attest:

HARRY F. MANBECK, JR.

Attesting Officer

Commissioner of Patents and Trademarks